(12) United States Patent
Wagle

(10) Patent No.: US 6,506,902 B2
(45) Date of Patent: Jan. 14, 2003

(54) SYNTHESIS OF THIAZOLIUM COMPOUNDS

(75) Inventor: Dilip Wagle, Pune (IN)

(73) Assignee: Alteon, Inc., Ramsey, NJ (US)

(*) Notice: Subject to any disclaimer, the term of this patent is extended or adjusted under 35 U.S.C. 154(b) by 0 days.

(21) Appl. No.: 09/821,846

(22) Filed: Mar. 29, 2001

(65) Prior Publication Data
US 2002/0013471 A1 Jan. 31, 2002

Related U.S. Application Data

(60) Provisional application No. 60/192,867, filed on Mar. 29, 2000.
(51) Int. Cl.$^7$ .............................................. C07D 277/24
(52) U.S. Cl. ...................................... 548/187; 548/204
(58) Field of Search ................................. 548/187, 204

(56) References Cited

U.S. PATENT DOCUMENTS 5,656,261 A * 8/1997 Cerami et al. ................. 424/53
5,853,703 A * 12/1998 Cerami et al. ................. 426/53

* cited by examiner

Primary Examiner—Joseph K. McKane
Assistant Examiner—Kamal Saeed
(74) Attorney, Agent, or Firm—Dechert

(57) ABSTRACT

Provided is a method of synthesizing a compound of formula I,

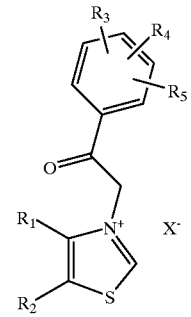

comprising:
(a) reacting a compound of formula II

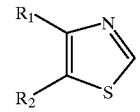

wherein $R_1$ and $R_2$ are independently hydrogen, hydroxy $(C_1-C_2)$alkyl, or $(C_1-C_2)$alkyl with,
a compound of formula III

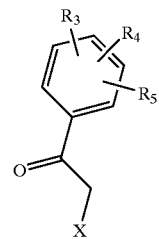

wherein
$R_3$, $R_4$, and $R_5$ are each independently of each other hydrogen, $(C_1-C_3)$alkyl, $(C_1-C_3)$alkoxy, or halogen; and
X is a leaving group,
in a solvent having a dielectric constant at 20° C. of at least 30 but no more than 40; and
(b) obtaining the compound I.

29 Claims, 2 Drawing Sheets

SYNTHESIS OF THIAZOLIUM COMPOUNDS

This application claims the priority of U.S. application Ser. No. 60/192,867, filed Mar. 29, 2000.

The present invention relates to methods of synthesizing certain thiazolium compounds.

In U.S. Pat. Nos. 5,656,261; 5,853,703; and 6,007,865 compounds were disclosed that are promising agents that can be used in compositions and methods useful in treating a number of indications. One mechanism of action contributing to these treatments is believed to be inhibition and reversal of nonenzymatic cross-linking (protein aging). These compounds can be used in therapeutic applications where proteins in the body deteriorate with age and as a consequence of diabetes.

Efficient syntheses for these compounds are desirable. Described herein is a surprisingly effective synthesis of a certain class of these compounds.

SUMMARY OF THE INVENTION

In one embodiment, the invention provides a method of synthesizing a compound of formula I,

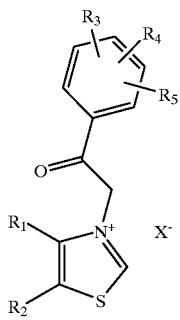

I comprising: reacting a compound of formula II

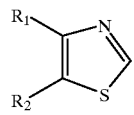

II wherein $R_1$ and $R_2$ are independently hydrogen, hydroxy $(C_1-C_2)$alkyl, or $(C_1-C_2)$alkyl with, a compound of the formula III

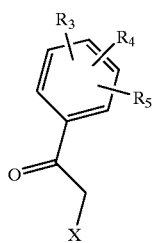

III wherein $R_3$, $R_4$, and $R_5$ are each independently of each other hydrogen, $(C_1-C_3)$alkyl, $(C_1-C_3)$alkoxy, or halogen; and X is a leaving group. The reaction is preferably conducted in a solvent having a dielectric constant at 20° C. of at least 30 but no more than 40.

In another embodiment, the invention provides a method of synthesizing a 4,5-dimethyl-3-(2-oxo-2-phenylethyl)-thiazolium salt comprising: reacting 4,5-dimethylthiazole with (IV), wherein X is a leaving group.

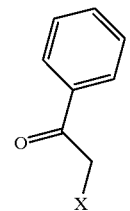

IV

DETAILED DESCRIPTION OF THE INVENTION

Figure 1:
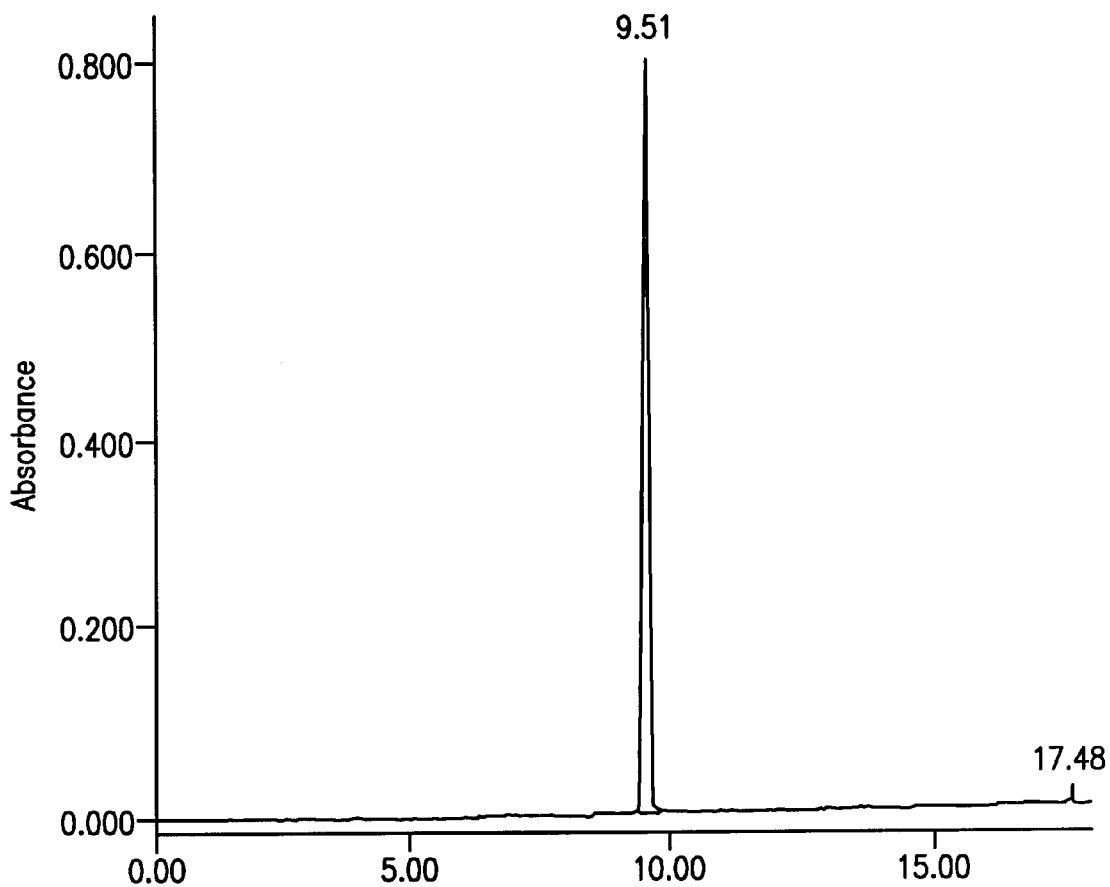
FIGS. 1 and 2 show HPLC analyses of product made according to the invention.

In accordance with the present invention, reaction and purification conditions have been developed that allow the preparation of N-alkyl thiazolium salts in high yield and of high purity. Useful methods described, for example, relate to the preparation of compounds of the formula I by reacting a compound of formula II with a compound of the formula III wherein X is a leaving group.

The solvent is selected to meet the characteristics described above, allowing the improved yields that can be obtained through the invention. Washing methods with appropriate solvents can also be selected to yield N-alkyl thiazolium salts with surprising purity from simple purification steps.

The leaving group referred to above preferably form a pharmaceutically or biologically acceptable anion upon alkylation of the thiazole moiety. Such anions include, for example, halides, for example, chlorides and bromides, tosylates, methanesulfonates, and mesitylenesulfonates. Other related leaving groups that are used preferably are those that form stable, non-toxic, and biologically or pharmaceutically acceptable salts upon alkylation of the thiazole moiety.

The solvents referred to above are dipolar solvents. These may include, for example, protic solvents, such as $C_2-C_3$ alcohols, and aprotic solvents, such as N-methylpyrrolidinone, dimethylformamide, dimethylacetamide, dimethyl sulfoxide, and acetonitrile. Solvents with dielectric constants at 20° C. above 30 but no more than 40 are preferred. Aprotic solvents are also preferred.

Preferably a solvent is selected so that the product thiazolium salt is only partially soluble. A solvent in which both the reactants are soluble but in which the thiazolium salt product is insoluble or only partially soluble is preferred. Acetonitrile is a preferred solvent.

The reaction is conducted at elevated temperatures such as 80° C. to 82° C. A preferred solvent is one that has a boiling point from 65° C. to 110° C. so that the reaction temperature can be conveniently and consistently maintained by refluxing the solvent. If the reaction mixture is refluxed a condenser should be used during the reaction. Typically the reaction is maintained at elevated temperatures for at least 24 hours. Preferably the temperature is maintained for at least 48 to 72 hours or from 80 to 100 hours, e.g. about 90 or 90.5 hours. The length of time will be dependent upon a number of factors, including temperature, concentration, and solvent.

Typically molar ratios of substituted acetophenone reagents/thiazoles combined in the reaction mixture are about 1:1 to 3:1. In some embodiments, ratios of about 1.5:1 to 2.5:1 (such as about 2:1) are useful.

A preferred method of conducting the reaction uses an inert atmosphere, for example using a blanket of nitrogen or argon gas. Additionally, the reaction is stirred or agitated using, for example, a mechanical stirring device.

Reaction progress can be followed by methods known to those in the art including chromatographic methods such as thin layer chromatography or HPLC. In solvents where the reaction begins to precipitate during heating, a specialized procedure for sampling the reaction mixture can be used. A slurry of the hot reaction mixture is filtered and the precipitate and/or filtrate are monitored by one of the chromatographic methods described above or, the slurry is dissolved in a stronger solvent and analyzed chromatographically. A preferred method is HPLC analysis when the reaction solvent used does not absorb a detecting-interfering amount of UV light at wavelengths where the products and reactants are detected.

To isolate the reaction product, the reaction mixture is cooled, for example, to a temperature of about 15° C. to 30° C., such as 22° C. to 25° C. Then, for example, an ethereal solvent is added, and the reaction product recovered by centrifugation or filtration. A preferred ethereal solvent is methyl tert-butyl ether.

The purification of the reaction product can include a recrystallization step. The process of selecting a suitable recrystallization solvent(s) is known to those in the art. Typically a solvent is chosen by consideration of a number of factors including maximization of the amount of purified, crystallized product when the crystallization mixture is cooled, and satisfactory solubility of the crude reaction product with the heated recrystallization solvent. Suitable recrystallization solvents include, for example, $C_1$–$C_3$ alcohols. 1:1 2:1, Further purification of the reaction product includes washing steps. A suitable wash solution would optimally dissolve maximal amounts of impurities while dissolving a minimal amount of the desired reaction product. A wash solution could be prepared from variable mixtures of two or more solvents. The wash solution can be, for example, a mixture of a $C_1$–$C_3$ alcohol and a $C_3$–$C_5$ ether. A preferred wash solution is a mixture of ethanol and methyl tert-butyl ether. The mixture of ethanol and ether is preferably a 2:8 to 4:6 (v/v) mixture and more preferably, a 25:75 to 35:65 (v/v) mixture.

The washing step can be performed after recovery of the reaction product on a filter. In addition, the washing cycle can be repeated, for example to achieve a higher purity of the product. Preferably the purity of the reaction product from the washing steps is at least 99.5% by isocratic reversed-phase HPLC analysis at 210 nm, preferably at least 99.7% or 99.8%. The washing step can further comprise suspending the reaction product in the washing solvent, agitating the resulting slurry, and recovering the product by filtration. Typically, the slurry is agitated at about 20° C. to 25° C.

The methods for isolation of the product described in the invention include drying steps. The compound can be, for example, dried at room temperature under vacuum, on trays lined with dryer paper.

Analytical methods for determining the purity of reaction product are known in the art. These include spectroscopic methods, for example, NMR spectroscopy and chromatographic methods. A preferred method of determining the purity of the product thiazolium salt is by application of HPLC techniques. While satisfactory analytical HPLC can be performed under a variety of conditions, preferred conditions include using a column with reversed phase packing such as 5μ ODS-2 (C-18) packing. For example, the 4.6×250 mm 5μ ODS-2 column from Metachem Technologies (Torrance, Calif.). Typically an isocratic solvent system is used to elute the sample, for example, a mobile phase containing 65% of an aqueous buffer of 10 mM 1-nonane sulfonic acid sodium salt and 50 mM sodium phosphate monobasic and 35% acetonitrile. The HPLC chromatogram is generated, for example, using a UV detector. Typical settings for analysis of the product thiazolium salt include monitoring at 210 nm or 252 nm.

Preferably, HPLC data is collected with data sampling at least as frequent as every 0.1 second periods. Preferably, the data is zeroed against a baseline run of the HPLC apparatus. Sensitivity or peak detection threshold is preferably set to a high sensitivity value that nonetheless allows data collection without spurious collection of detector or electronic noise. For example, using Rainin Dynamax R software (version 1.4) to collect the data, and Rainin Dynamax Mode UV-1 UV/visible variable wavelength detector, minimum peak detection sensitivity can be set at 10–50 millivolt/second or lower.

Figure 2:
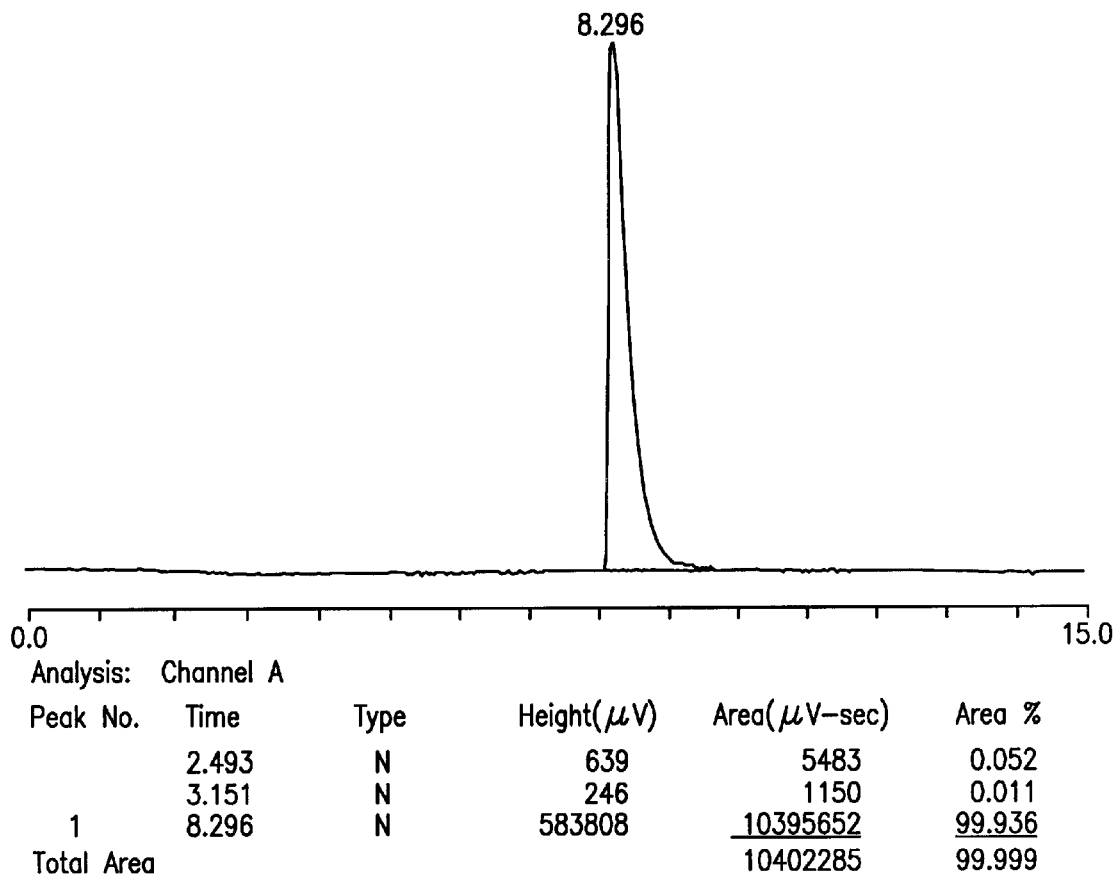

FIG. 1 shows an analysis of a batch of 4,5-dimethyl-3-(2-oxo-2-phenylethyl)-thiazolium chloride as analyzed by a gradient HPLC method that uses a 25 to 50% acetonitrile gradient. FIG. 2 shows an isocratic analysis (35% acetonitrile, v/v). HPLC chromatographs were developed in 50 mM $NaH_2PO_4$, 10 mM 1-nonane sulfonic acid Detection was at 210 nm.

The yield of the product from the above conditions is high (e.g. 70% overall, or higher). The product can be obtained at high purity using the methods here described (>99.5% as determined by HPLC). Additionally, the process is convenient for preparing thiazolium salts on a commercial scale.

The following example further illustrate the present invention, but of course, should not be construed as in any way limiting its scope.

EXAMPLE 1
Preparation of 4,5-Dimethyl-3-(2-oxo-2-phenylethyl)-thiazolium chloride A reactor equipped with an agitator and a condenser was charged with 37.47 kg of acetonitrile, and purged with nitrogen. A blanket of nitrogen was maintained during the reaction. Agitation was started and 9.52 kg of 4,5-dimethylthiazole (84.1 mmol) and 13.00 kg of 2-chloroacetophenone (84.1 mmol) were added into the reactor. The mixture was agitated and heated to reflux (81° C.). Refluxing was maintained at this temperature for about 96.5 hours. The reaction was monitored by HPLC for the presence of 4,5-dimethyl-3-(2-oxo-2-phenylethyl)-thiazolium chloride in the refluxate. The product precipitated out of the hot reaction mixture during reflux. After 3 days a sample of hot reaction slurry was filtered, and washed with a mixture of absolute ethanol and methyl tert-butyl ether (3:7). An HPLC analysis of this sample showed no detectable amounts of starting materials.

The reaction was cooled to 20° C. to 25° C. and 33.7 kg of methyl tert-butyl ether was added. The batch was agitated at 20° C. to 25° C. for about 3 hours. Part of the mixture was isolated in the centrifuge; the remaining product was agitated overnight and was isolated by filtering through a large buchner funnel fitted with Whatman # 1 filter paper. The product from the centrifuge was transferred to the top of the cake in the buchner funnel. The reactor (R-2) was rinsed with 20 L of methyl tert-butyl ether onto the product cake. The filtered cake was washed three times with a wash solution containing a mixture of 4.17 kg of absolute ethanol and 9.74 kg of methyl tert-butyl ether. The wet solid (20.07 kg) was transferred to the drying trays. The product was evenly distributed on the trays and dried at room temperature under vacuum (25.6" Hg) for 18 hours. The dry weight of the 4,5-dimethyl-3-(2-oxo-2-phenylethyl)-thiazolium chloride was 17.99 kg.

Crude 4,5-dimethyl-3-(2-oxo-2-phenylethyl)-thiazolium chloride was recrystallized by charging the crude 4,5-dimethyl-3-(2-oxo-2-phenylethyl)-thiazolium chloride into a reactor equipped with a condenser and an agitator. Absolute ethanol 37.19 kg was added and agitation was started. The reactor was purged with nitrogen and a nitrogen blanket was maintained during the processing. The mixture was heated to gentle reflux and maintained at 78° C. until a complete solution was attained. From the bottom outlet of the reactor to the inlet of another reactor, a 0.5 micron in-line cartridge filter was set up using an appropriate pump. When the batch was in solution, the filter cartridge, pump, and lines were preheated with the hot absolute ethanol in the first reactor. The batch was filtered into the new reactor. Absolute ethanol (4.2 kg) was used to rinse the first reactor into the reactor containing the filtrate. The batch was cooled to 20° C. to 25° C. and agitated at this temperature overnight. The product was filtered through a large Buchner funnel fitted with a Whatman No. 1 filter paper. The filtered cake was washed with a wash solution containing a mixture of 5.80 kg of absolute ethanol and 13.52 kg of methyl tert-butyl ether. The wet 4,5-dimethyl-3-(2-oxo-2-phenylethyl)-thiazoliurn chloride (14.36 kg) was transferred in the trays lined with dryer paper. The product was distributed evenly on the trays. 4,5-Dimethyl-3-(2-oxo-2-phenylethyl)-thiazolium chloride was dried at room temperature under vacuum (25.9" Hg) about 23 hours to a constant weight (12.21 kg, 54.22%) (Lot A). 4,5-Dimethyl-3-(2-oxo-2-phenylethyl)-thiazolium chloride (Lot A) was further purified through washing. Methyl tert-butyl ether 18.9 kg and absolute ethanol 8.0 kg were added to a reactor equipped with a condenser and an agitator. The reactor was purged with nitrogen and a nitrogen blanket was maintained during the processing. 4,5-Dimethyl-3-(2-oxo-2-phenylethyl)-thiazolium chloride (Lot. A) 11.9 kg was charged into the reactor and the agitator started. The slurry was stirred at 20° C. to 25° C. for about 30 minutes. The product was filtered through a large buchner funnel fitted with a Whatman No. 1 filter paper. The filtered cake was washed with a wash solution containing a mixture of 1.3 kg of absolute ethanol and 3.2 kg of methyl tert-butyl ether. The wet 4,5-dimethyl-3-(2-oxo-2-phenylethyl)-thiazolium chloride (13.4 kg) was transferred to the trays lined with dryer paper. The product was distributed evenly on the trays. 4,5-Dimethyl-3-(2-oxo-2-phenylethyl)-thiazolium chloride was dried at room temperature under vacuum (25.9" Hg) about 2 hours to a constant weight. The dryer was unloaded into a tared, polyethylene bag-lined drum or pail. (11.8 kg, 99.2% from Lot No. A; 52.40% overall yield (Lot No. B).

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of synthesizing a compound of formula I,

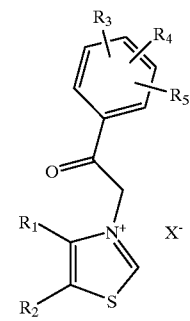

comprising:
(a) reacting a compound of formula II

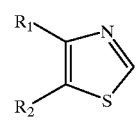

wherein $R_1$ and $R_2$ are independently hydrogen, hydroxy $(C_1-C_2)$alkyl, or $(C_1-C_2)$alkyl
with,
a compound of formula III

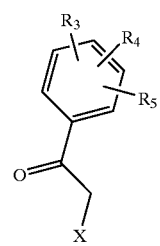

wherein
$R_3$, $R_4$, and $R_5$ are each independently of each other hydrogen, $(C_1-C_3)$alkyl, $(C_1-C_3)$alkoxy, or halogen; and
X is a leaving group,
in a solvent having a dielectric constant at 20° C. of at least 30 but no more than 40, and wherein the solvent and amount of solvent dissolve compounds II and III, but precipitate at least a portion of the compound of formula I during the reacting step; and
(b) obtaining the compound of formula I.

2. The method of claim 1, wherein the amount of solvent is selected to dissolve compounds II and III, but precipitate at least a portion of the compound of formula I during the reacting step.

3. The method of claim 1, wherein the amount of solvent is selected to precipitate an amount of the compound I equal to at least 20% of the theoretical yield.

4. The method of claim 1, wherein the solvent is aprotic.

5. The method of claim 1, wherein the solvent is acetonitrile.

6. The method of claim 1, wherein the reacting step is conducted at elevated temperatures maintained for at least 24 hours.

7. The method of claim 1, wherein the reacting step is conducted at reflux.

8. The method of claim 1, further comprising:
(c) re-crystallizing the product;
(d) washing the re-crystallized product by suspending it in a mixture of a $C_1$ to $C_3$ alcohol and a $C_3$ to $C_5$ ether; and
(e) recovering the product,
wherein the alcohol/ether mixture, time of suspension, and an election to conduct a total of one to three iterations of steps (d) and (e) are selected to achieve at least 95% yield from the crystallized product of step (c) and a purity of at least 99.5% by isocratic, reversed-phase HPLC analysis monitored at 210 nm.

9. The method of claim 8, wherein the re-crystallized product is suspended in a mixture of ethanol and methyl tert-butyl ether.

10. The method of claim 9, wherein the mixture is a 2:8 to 4:6 (v/v) mixture, respectively.

11. The method of claim 10, wherein the mixture is a 25:75 to 35:65 (v/v) mixture.

12. The method of claim 1, further comprising:
(c) re-crystallizing the product;
($d^1$) washing the re-crystallized product by suspending it in a 2:8 to 4:6 (v/v) mixture of a $C_1$ to $C_3$ alcohol and a $C_3$ to $C_5$ ether; and
(e) recovering the product.

13. The method of claim 1, comprising synthesizing a compound of formula I, wherein $R_1$ and $R_2$ are not both hydrogen.

14. A method of synthesizing a 4,5-dimethyl-3-(2-oxo-2-phenylethyl)-thiazolium salt comprising:
(a) reacting 4,5-dimethylthiazole with (IV), wherein X is a leaving group,

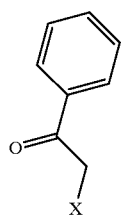

IV in a solvent having a dielectric constant at 20° C. of at least 30 but no more than 40,
wherein the amount of solvent dissolves compounds (a) and (b), but precipitates at least a portion of the 4,5-dimethyl-3-(2-oxo-2-phenylethyl)-thiazolium salt during the reacting step; and
(b) obtaining the 4,5-dimethyl-3-(2-oxo-2-phenylethyl)-thiazolium product.

15. The method of claim 14, wherein the amount of solvent is selected to dissolve compounds (a) and (b), but precipitate at least a portion of the 4,5-dimethyl-3-(2-oxo-2-phenylethyl)-thiazolium salt during the reacting step.

16. The method of claim 14, wherein the amount of solvent is selected to precipitate an amount of the 4,5-dimethyl-3-(2-oxo-2-phenylethyl)-thiazolium salt equal to at least 20% of the theoretical yield.

17. The method of claim 14, wherein the solvent is aprotic.

18. The method of claim 14, wherein the solvent is acetonitrile.

19. The method of claim 14, wherein the reacting step is conducted at elevated temperature maintained for at least 24 hours.

20. The method of claim 14, wherein the reacting step is conducted at reflux.

21. The method of claim 14, further comprising:
(c) re-crystallizing the product;
(d) washing the re-crystallized product by suspending it in a mixture of a $C_1$ to $C_3$ alcohol and a $C_3$ to $C_5$ ether; and
(e) recovering the product,
wherein the alcohol/ether mixture, time of suspension, and an election to conduct a total of one to three iterations of steps (d) and (e) are selected to achieve at least 95% yield from the crystallized product of step (c) and a purity of at least 99.5% by isocratic, reversed-phase HPLC analysis monitored at 210 nm.

22. The method of claim 21, wherein the re-crystallized product is suspended in a mixture of ethanol and methyl tert-butyl ether.

23. The method of claim 22, wherein the mixture is a 2:8 to 4:6 (v/v) mixture, respectively.

24. The method of claim 23, wherein the mixture is a 25:75 to 35:65 (v/v) mixture.

25. The method of claim 14, further comprising:
(c) re-crystallizing the product;
(d) washing the re-crystallized product by suspending it in a 2:8 to 4:6 (v/v) mixture of a $C_1$ to $C_3$ alcohol and a $C_3$ to $C_5$ ether; and
(e) recovering the product.

26. The method of claim 6, wherein the reacting step is conducted at reflux.

27. The method of claim 26, wherein the reaction time is selected based on monitoring reaction progress.

28. The method of claim 27, wherein the solvent is acetonitrile.

29. The method of claim 28, wherein the molar ratio of the compound of the formula III to the compound of formula II is about about 1:1 to 3:1.

* * * * *